(12) United States Patent
Truschel et al.

(10) Patent No.: US 12,233,210 B2
(45) Date of Patent: Feb. 25, 2025

(54) METHOD OF DELIVERING VARIABLE VENTILATION WITH AVAPS

(71) Applicant: KONINKLIJKE PHILIPS N.V., Eindhoven (NL)

(72) Inventors: William Truschel, Monroeville, PA (US); Pablo Andres Ñañez Ojeda, Monroeville, PA (US); Francesco Vicario, Boston, MA (US); Michael Polkey, Monroeville, PA (US); Nikolaos Karamolegkos, Boston, MA (US)

(73) Assignee: Koninklijke Philips N.V., Eindhoven (NL)

( * ) Notice: Subject to any disclaimer, the term of this patent is extended or adjusted under 35 U.S.C. 154(b) by 961 days.

(21) Appl. No.: 17/317,031

(22) Filed: May 11, 2021

(65) Prior Publication Data

US 2021/0386948 A1  Dec. 16, 2021

Related U.S. Application Data

(60) Provisional application No. 63/037,620, filed on Jun. 11, 2020.

(51) Int. Cl.
*A61M 16/10* (2006.01)
*A61M 16/00* (2006.01)

(52) U.S. Cl.
CPC ........ *A61M 16/024* (2017.08); *A61M 16/105* (2013.01); *A61M 2205/502* (2013.01)

(58) Field of Classification Search
CPC ... A61B 5/087; A61M 16/00; A61M 16/0003; A61M 16/0051; A61M 16/0063;
(Continued)

(56) References Cited

U.S. PATENT DOCUMENTS

| 5,582,163 A | 12/1996 | Bonassa |
| 8,746,247 B2 | 6/2014 | Mechlenburg |

(Continued)

OTHER PUBLICATIONS

International Search Report for PCT/EP2021/065402 filed Jun. 9, 2021.
(Continued)

*Primary Examiner* — Annette Dixon
(74) *Attorney, Agent, or Firm* — Daniel H. Brean; Andrew M. Gabriel

(57) ABSTRACT

A method for controlling a ventilator to provide variable volume (VV) with average volume assured pressure support (AVAPS), including: producing a VV target volume using a VV distribution function; producing a volume error Verror that is the difference between the VV target volume and a measured volume of the previous breath; scaling the volume error Verror; producing a VV target difference as the difference between VV target volume and the VV target volume of the previous breath; producing a modified volume error by adding the VV target difference to the scaled volume error Verror; producing a delta pressure support ΔPS based upon the modified volume error and a dynamic compliance; and producing a current pressure support value based upon the delta pressure support ΔPS and the pressure support value of the previous breath.

18 Claims, 6 Drawing Sheets

(58) Field of Classification Search
CPC ............ A61M 16/0069; A61M 16/024; A61M 16/026; A61M 16/06; A61M 16/0833; A61M 16/0875; A61M 16/0883; A61M 16/20; A61M 16/204; A61M 2016/0027; A61M 2016/0033; A61M 2016/0039; A61M 2016/0042; A61M 2202/0208; A61M 2202/025; A61M 2205/15; A61M 2205/18; A61M 2205/3331; A61M 2205/50; A61M 2205/502; A61M 2205/505; A61M 2205/583; A61M 2230/005; A61M 2230/06; A61M 2230/205; A61M 2230/40; A61M 2230/42

See application file for complete search history.

(56) References Cited

U.S. PATENT DOCUMENTS

| | | | |
|---|---|---|---|
| 9,717,868 B2 | 8/2017 | Truschel | |
| 2007/0089738 A1* | 4/2007 | Soliman | A61M 16/026 128/202.22 |
| 2007/0101992 A1* | 5/2007 | Soliman | A61M 16/026 128/204.21 |
| 2009/0241962 A1* | 10/2009 | Jafari | A61M 16/06 128/205.25 |
| 2011/0214672 A1* | 9/2011 | Soliman | A61M 16/026 128/204.23 |
| 2012/0000468 A1 | 1/2012 | Milne | |
| 2012/0266882 A1 | 10/2012 | Dellaca | |
| 2015/0107584 A1* | 4/2015 | Jafari | A61M 16/026 128/202.22 |
| 2016/0287824 A1* | 10/2016 | Chang | A61M 16/0066 |
| 2019/0151601 A1 | 5/2019 | Bonassa | |
| 2021/0393902 A1* | 12/2021 | Dong | A61M 16/0003 |

OTHER PUBLICATIONS

Karin, J. et al., "Treatment of sleep-disordered breathing with positive airway pressure devices: technology update", Medical Devices: Evidence and Research, Oct. 1, 2015, p. 425.

Lefevre, G.R., et al., "Improved arterial oxygenation after oleic acid lung injury in the pig using a computer-controlled mechanical ventilator." Am J Respir Crit Care Med, 1996. Abstract.

Suki. B., et al., "Life-support system benefits from noise." Nature, 1998. 393(6681): p. 127-8).

Limsuwat, C. et al., "Effect of non-invasive mechanical ventilation with average vol. assured pressure support (AVAPS) in patients with chronic obstructive pulmonary disease with acute exacerbation: A randomized pilot trial". Pilot Study. The Southwest Respiratory and Critical Care Chronicles 2019:7(30):19-28.

Mutch, W.A., et al., "Biologically variable or naturally noisy mechanical ventilation recruits atelectatic lung." Am J Respir Crit Care Med, 2000. 162(1): p. 319-23.

Arold, S.P., et al., "Variable tidal volume ventilation improves lung mechanics and gas exchange in a rodent model of acute lung injury." Am J Respir Crit Care Med, 2002. 165(3): p. 366-71.

Arold, S.P., et al., "Variable ventilation induces endogenous surfactant release in normal guinea pigs." Am J Physiol Lung Cell Mol Physiol, 2003. 285(2): p. L370-5.

Suki, B., et al., "Regulatory Roles of Fluctuation-Driven Mechanotransduction in Cell Function." Physiology (Bethesda), 2016. 31(5): p. 346-58.

Bellardine, C.L., et al., "Comparison of variable and conventional ventilation in a sheep saline lavage lung injury model." Crit Care Med, 2006. 34(2): p. 439-45.

Arold, S.P. et al., "Variable stretch pattern enhances surfactant secretion in alveolar type II cells in culture." Am J Physiol Lung Cell Mol Physiol, 2009. 296(4): p. L574-81.

Thammonomai, A., et al., "Combined effects of ventilation mode and positive end-expiratory pressure on mechanics, gas exchange and the epithelium in mice with acute lung injury." PLoS One, 2013. 8(1): p. e53934.

Thammonomai, A., et al., "Design of a new variable-ventilation method optimized for lung recruitment in mice." J Appl Physiol, 2008. 104(5): p. 1329-40.

Bartolak_Suki, E., et al., "Optimization of Variable Ventilation for Physiology, Immune Response and Surfactant Enhancement in Preterm Lambs." Front Physiol, 2017. 8: p. 425.

Bartolak_Suki, E., et al., "Fluctuation-driven mechanotransduction regulates mitochondrial-network structure and function." Nat Mater, 2015. 14(10): p. 1049-57.

Berry, C.A., et al., "Variable ventilation enhances ventilation without exacerbating injury in preterm lambs with respiratory distress syndrome." Pediatr Res, 2012. 72(4): p. 384-92.

Camilo, L.M., et al., "Positive end-expiratory pressure and variable ventilation in lung-healthy rats under general anesthesia." PLoS One, 2014. 9(11): p. e110817.

De Magalhaes, R.F., et al., "Variable ventilation improves pulmonary function and reduces lung damage without Increasing bacterial translocation in a rat model of experimental pneumonia." Respir Res, 2016. 17(1): p. 158.

Henriques, I., et al., "Comparison between Variable and Conventional vol. Controlled Ventilation on Cardiorespiratory Parameters in Experimental Emphysema." Front Physiol, 2016. 7: p. 277.

Wang, R. et al., "Variable lung protective mechanical ventilation decreases incidence of postoperative delirium and cognitive dysfunction during open abdominal surgery." Int J Clin Exp Med, 2015. 8(11): p. 21208-14.

* cited by examiner

METHOD OF DELIVERING VARIABLE VENTILATION WITH AVAPS

CROSS-REFERENCE TO RELATED APPLICATIONS

This patent application claims the priority benefit under 35 U.S.C. § 119 (e) of U.S. Provisional Application No. 63/037,620, filed on Jun. 11, 2020, the contents of which are herein incorporated by reference.

TECHNICAL FIELD

Various exemplary embodiments disclosed herein relate generally to a system and method for delivering variable ventilation with average volume assured pressure support (AVAPS).

BACKGROUND

Variable ventilation has been clinically proven to improve cell health in mechanically ventilated patients. This mode of ventilation intentionally varies the size of individual breaths but keeps the average breath size constant. AVAPS is a mode that allows volume target ventilation to be delivered to chronic patients with an noninvasive ventilation (NIV) interface. AVAPS is beneficial for spontaneously breathing patients because it limits the pressure and does not overreact to occasional events like swallowing, coughing, glottic closure, speaking, and movement.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a method for controlling a ventilator to provide variable volume (VV) with average volume assured pressure support (AVAPS), including: producing a VV target volume using a VV distribution function; producing a volume error Verror that is the difference between the VV target volume and a measured volume of the previous breath; scaling the volume error Verror; producing a VV target difference as the difference between VV target volume and the VV target volume of the previous breath; producing a modified volume error by adding the VV target difference to the scaled volume error Verror; producing a delta pressure support ΔPS based upon the modified volume error and a dynamic compliance; and producing a current pressure support value based upon the delta pressure support ΔPS and the pressure support value of the previous breath.

Various embodiments are described, wherein producing a delta pressure support ΔPS further comprises dividing the modified volume error by the dynamic compliance.

Various embodiments are described, wherein the volume error Verror is scaled by a factor of 2.

Various embodiments are described, further comprising limiting the current pressure support by a minimum pressure support value and a maximum pressure support value.

Various embodiments are described, further comprising generating a breath profile based upon the current pressure support and a positive end-expiratory pressure (PEEP) value.

Various embodiments are described, further comprising rise time filtering the breath profile.

Various embodiments are described, further comprising applying the breath profile to a user's lung and measuring a volume of the resulting breath.

Various embodiments are described, wherein the VV distribution function has a mean value based upon a received target volume value.

Various embodiments are described, wherein the VV distribution function may be selected from a plurality of different VV distribution functions.

Further various embodiments relate to a controller configured to control a ventilator to provide variable volume (VV) with average volume assured pressure support (AVAPS), including: a memory; a processor coupled to the memory, wherein the processor is further configured to: produce a VV target volume using a VV distribution function; produce a volume error Verror that is the difference between the VV target volume and a measured volume of the previous breath; scale the volume error Verror; produce a VV target difference as the difference between VV target volume and the VV target volume of the previous breath; produce a modified volume error by adding the VV target difference to the scaled volume error Verror; produce a delta pressure support ΔPS based upon the modified volume error and a dynamic compliance; and produce a current pressure support value based upon the delta pressure support ΔPS and the pressure support value of the previous breath.

Various embodiments are described, wherein producing a delta pressure support ΔPS further comprises dividing the modified volume error by the dynamic compliance.

Various embodiments are described, wherein the volume error Verror is scaled by a factor of 2.

Various embodiments are described, wherein the processor is further configured to limit the current pressure support by a minimum pressure support value and a maximum pressure support value.

Various embodiments are described, wherein the processor is further configured to generate a breath profile based upon the current pressure support and a positive end-expiratory pressure (PEEP) value.

Various embodiments are described, wherein the processor is further configured to rise time filter the breath profile.

Various embodiments are described, wherein the processor is further configured to apply the breath profile to a user's lung and measuring a volume of the resulting breath.

Various embodiments are described, wherein the VV distribution function has a mean value based upon a received target volume value.

Various embodiments are described, wherein the VV distribution function may be selected from a plurality of different VV distribution functions.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Figure 1:
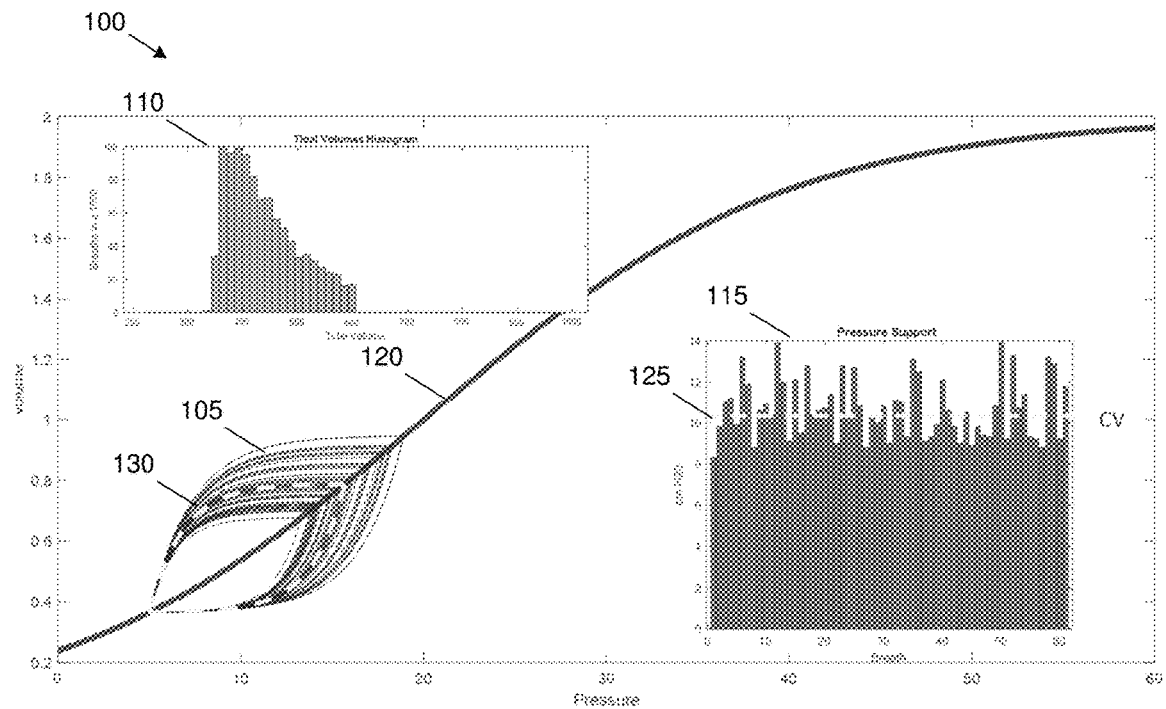
FIG. 1 illustrates a plot of lung volume vs pressure showing the variable loops that are made during VV with AVAPS along with the variable pressure support.

Variable ventilation delivers tidal volumes (TV) that vary from breath to breath around a prescribed average TV in accordance with a predefined statistical distribution. FIG. 1 illustrates a pressure-volume plot 100 of 1000 variable volume breaths illustrated by varying the pressure support. The pressure-volume plot 100 includes line 120 that illustrates the general relationship between pressure and volume for the lung from total collapse to full distension. The pressure-volume plot 100 shows various PV loops 105 that are produced by this manner of ventilation, where each loop illustrates the pressure and volume values during a breath. A histogram plot 110 displayed on top of the pressure-volume plot 100 shows a histogram of how TV is distributed over a 1000 breath sequence. For conventional mechanical ventilation (MV) a dotted loop 130 is shown where the TV is a constant value CV. The pressure support required to produce this constant value is shown as a dotted line 125 in pressure support plot 115 (which is also displayed on top of the pressure-volume plot 100). For VV, the vertical bars in pressure support plot 115 shows how the pressure support for each breath varies to produce the desired variation in TV according to histogram plot 110 and the relationship between pressure and volume 120. More specifically, VV delivers variable TVs with each breath with the mean equal to the TV that would be prescribed in conventional MV. The intuition behind this ventilation strategy comes from the observation that biological systems exhibit intrinsic fluctuations. Subsystems like the cardiovascular and respiratory systems exhibit variability even during steady-state conditions. Breath-by-breath variation in tidal volume and respiratory rate contribute to sustain fast state transition while minimizing the ratio between tissue stress and strain. The coefficient of variation in tidal volume in healthy spontaneous breathing at rest is approximately 33%. Lefevre et al. were the first to conjecture that the use of physiological variability in the respiratory pattern, as observed in the healthy resting state, may be beneficial in patients under controlled mechanical ventilation, to improve lung function and reduce injury in the diseased lung. (See Lefevre, G. R., et al., Improved arterial oxygenation after oleic acid lung injury in the pig using a computer-controlled mechanical ventilator. Am J Respir Crit Care Med, 1996. 154(5): p. 1567-72)

Further research has demonstrated that VV is superior to conventional MV currently in clinical use, with improved outcomes and reduced likelihood of ventilator-induce lung injury (VILI). VV delivers a specific set of TVs and respiratory frequencies (f) such that TVs are pulled from a specific probability distribution optimized to best recruit the lung's collapsed regions, and f is matched so that the delivered minute ventilation is constant. This research has illustrated that VV improves gas exchange and reduces lung injury compared to conventional MV. VV may use the following mechanisms to improve performance as compared to conventual MV: VV maintains an open lung; VV promotes surfactant production and release; and VV downregulates inflammation in the lung.

In previous studies, VV has only been implemented in the acute setting with volume control ventilation (VCV) where the volume control setpoint is varied breath by breath according to the distribution profile of Suki, et al. (See Suki, B., et al., *Life-support system benefits from noise.* Nature, 1998. 393 (6681): p. 127-8).

Pressure control ventilation (PCV) has become the preferred method of chronically ventilated patients because it prevents barotrauma and discourages asynchrony during the periods of bulbar activity, cough, glottic movements and activity. Volume assured pressure support (VAPS) modes are a hybrid mix of the VCV and PCV where the ventilator will target a volume setpoint through successive small changes in pressure support, but maintain the control pressure within limits set by the clinician to optimize patient comfort and safety. VAPS has also been demonstrated to be effective in noninvasive ventilation because it has algorithms that are leak compensated and tolerant of variable leak. However, the slow reaction of VAPS to changing respiratory physiology makes it inherently difficult to target the programmed variation of the target volume Vt such as in VV unless the VAPS mode is modified at its core to support VV.

Embodiments of a method for providing average volume assured pressure support (AVAPS) are described that combines the algorithms of VV and AVAPS to produce a VV algorithm that performs as closely as possible to that demonstrated in previous studies with modified control ventilation (CV) for VV. Embodiments of a system for implementing the method are also described. The method and system described strive to maintain the comfort and protection and all of the other benefits of the AVAPS mode in the chronic patient with the benefit of open lung and cell health of VV.

Figure 2:
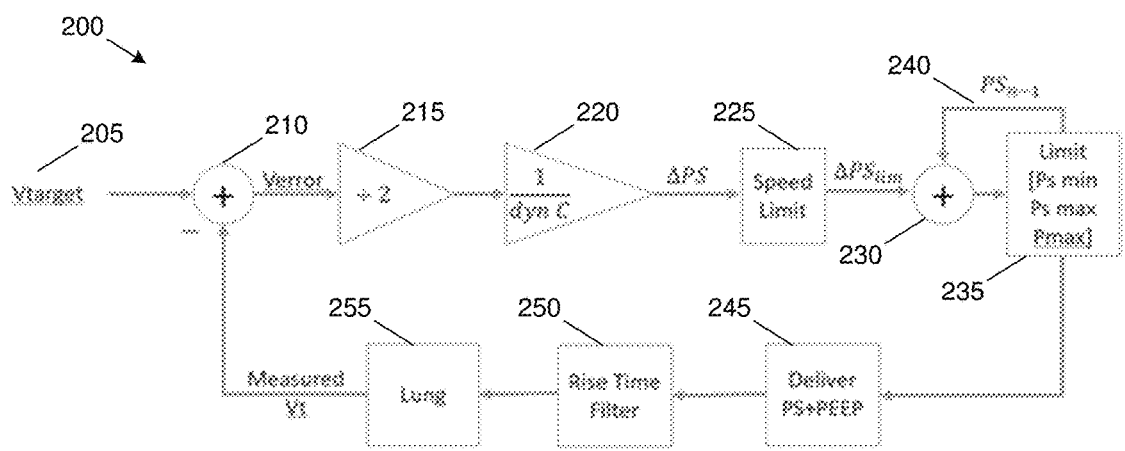
FIG. 2 illustrates a block diagram of a first AVAPS method.

AVAPS seeks to target a set tidal volume by adjusting pressure support in a systematic method. FIG. 2 illustrates a block diagram of a first AVAPS method 200. First, the first AVAPS method 200 computes the volume error Verr as the difference (using adder 210) between the measured tidal volume Vt and the target volume Vtarget 205 on each breath. A divider 215 divides the error Verror in half. It is noted that the error Verror may be divided by other values as well to provide stability and robustness in the presence of noise or disturbances. This factor determines the gain of the adjustment controller. The output of the divider 215 is then attenuated by the ventilator's best estimate of the dynamic compliance dyn C using the attenuator 220 to determine a change in pressure support ΔPS to be applied to achieve the change in volume. The dynamic compliance dyn C is defined as the change in lung volume per unit change in the pressure support. A speed limiter 225 limits the pressure support ΔPS so that ΔPS can only change so fast resulting in $\Delta PS_{lim}$. An adder 230 adds limited pressure support $\Delta PS_{lim}$ to the previous pressure support value $PS_{n-1}$. The updated pressure support value is then limited 235 based upon the minimum and maximum pressure support values allowed for the user. This limited pressure support value is then used to generate a breath profile to deliver the specified pressure support and positive end-expiratory pressure (PEEP) 245. For example, if the PEEP value of 5 cm H₂O pressure with a PS of 12 cm H₂O is specified, a breath profile that starts at 5 cm H₂O pressure and rises to 17 cm H₂O pressure will be generated. A rise time filter 250 may be used to further smooth the waveform used to generate the breath, and the rise time filter 250 may be, for example, a low pass filter. The lung is monitored and the tidal volume Vt is measured 255, and this is the value that is fed back to the adder 210.

The relationship between tidal volume delivery and pressure support when updating the first AVAPS method 200 to accommodate variable ventilation will first be explained. The expected closed form relationship between flow in the inspiratory phase to a passive lung and pressure support is given by the following equation:

$$Q(t) = \left(\frac{PS \cdot c}{\tau - RC}\right) \cdot (e^{T/\tau} - e^{-T/RC}),$$

where, PS is the delivered pressure support, C is the compliance of the lung, R is the resistance of the lung, τ is the time constant of the rise time filter, and Q (t) is the patient flow over time. The volume at the end of inspiration is approximated by the following equation:

$$Vt(t) = \left(\frac{-PS \cdot C \cdot \tau}{\tau - RC}\right) \cdot (e^{-t/\tau}) + \left(\frac{PS \cdot R \cdot C^2 \cdot \tau}{\tau - RC}\right) \cdot (e^{-t/RC}) + PS \cdot C.$$

The above equation indicates that the volume delivered is linearly proportional to pressure support. Note that no closed form equation exists when the patient is active, but the assumption is that for neuromuscular patients, the majority of volume results from ventilator assistance.

Figure 3:
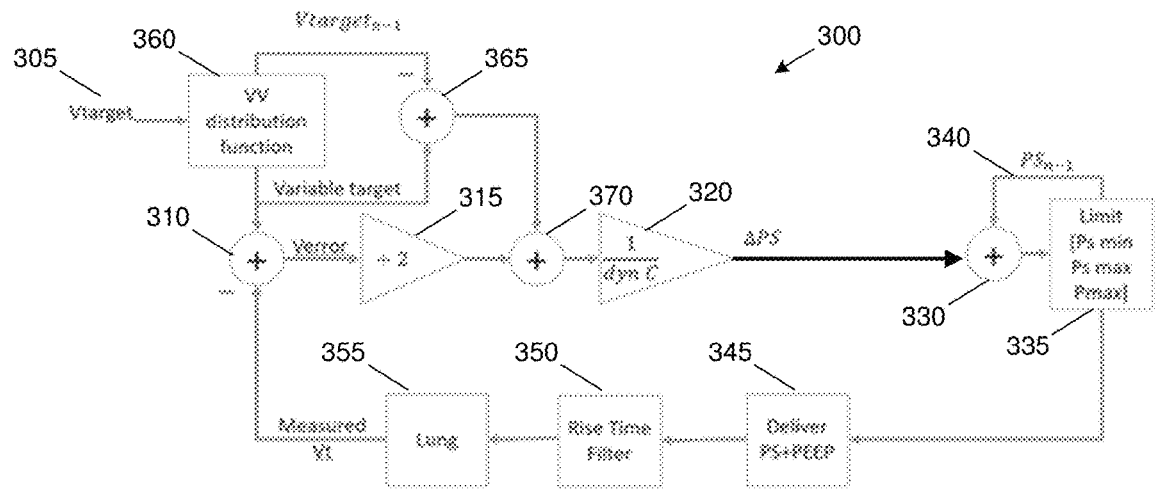
FIG. 3 illustrates an embodiment of a second AVAPS method that supports variable ventilation.

This implies that the first AVAPS method 200 of FIG. 2 may be modified to support variable ventilation. FIG. 3 illustrates an embodiment of a second AVAPS method 300 that supports variable ventilation. First, the second AVAPS method 300 receives the target volume Vtarget 305. A VV distribution function 360 produces a variable target volume with Vtarget as the mean value. The second AVAPS method 300 computes the volume error Verr as the difference (using adder 310) between the measured tidal volume Vt and the variable target volume on each breath. A divider 315 divides the error Verror in half. It is noted that the error Verror may be divided by other values as well to provide stability and robustness in the presence of noise or disturbances. This factor determines the gain of the adjustment controller. An adder 365 further determines the change in target volume by subtracting the previous target volume value $Vtarget_{n-1}$ from the current variable target value. An adder 370 adds the difference value output by the adder 365 to the output of the divider 315. The output of the adder 370 is then attenuated by the ventilator's best estimate of the dynamic compliance dyn C using the attenuator 320 to result in a change in pressure support ΔPS to be applied to achieve the change in volume. An adder 330 adds pressure support change ΔPS to the previous pressure support value $PS_{n-1}$. The updated pressure support value is then limited 335 based upon the minimum and maximum pressure support values allowed for the user. This limited pressure support value is then used to generate a breath profile to deliver the specified pressure support and positive end-expiratory pressure (PEEP) 345. For example, if the PEEP value of 5 cm H₂O pressure with a PS of 12 cm H₂O pressure is specified, a breath profile that starts at 5 cm H₂O pressure and rises to 17 cm H₂O pressure will be generated. A rise time filter 350 may be used to further smooth the waveform used to generate the breath, and the rise time filter 350 may be, for example, a low pass filter. The lung is monitored and the tidal volume Vt is measured 355, and this is the value that is fed back to the adder 310.

It is noted that the speed limiter of the first AVAPS method 200 in FIG. 2 is removed in the second AVAPS method 300 to allow volume to vary breath to breath, but the main components including the pressure limiter are otherwise preserved. The target is no longer a constant volume, but a volume that is varied according to the prescribed distribution function.

Figure 4A:
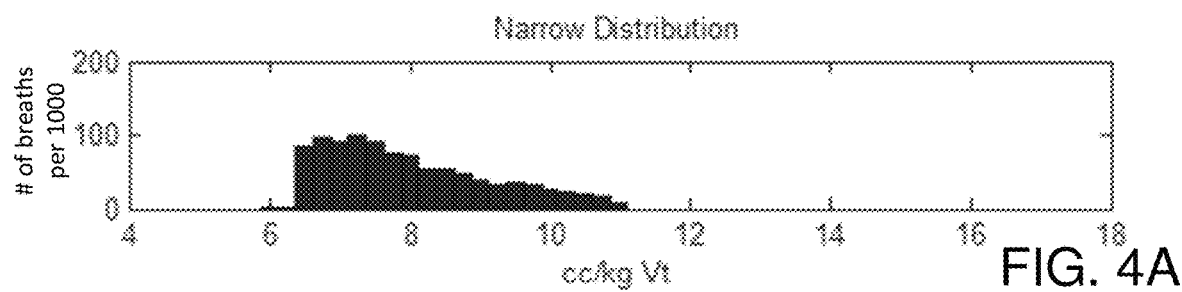
FIGS. 4A, 4B, and 4C are histogram plots of the number of breaths per 1000 breaths at various volumes Vt for narrow, medium, and wide distributions respectively.
Figure 4B:
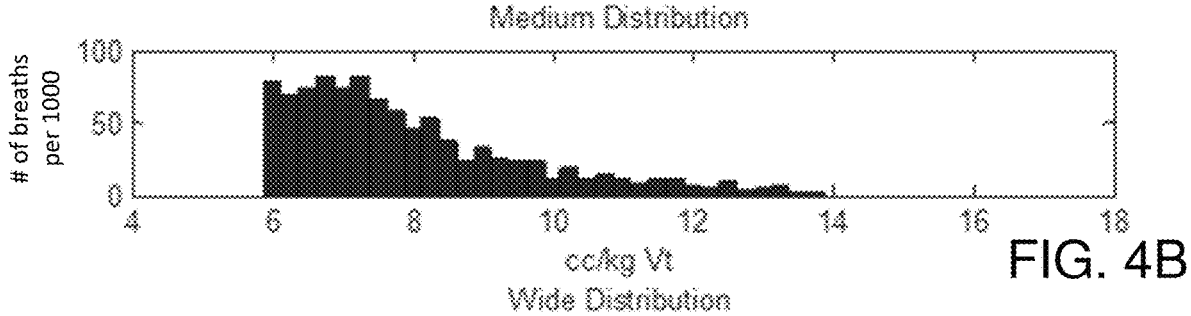
Figure 4C:
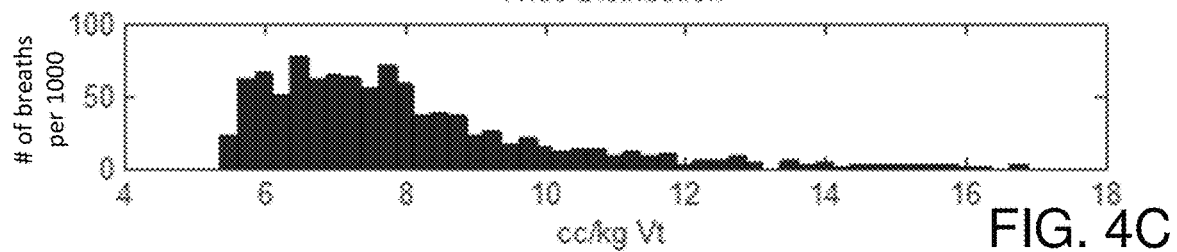

Professor Bela Suki of Boston University has produced 3 distribution functions to be considered for variable ventilation. FIGS. 4A, 4B, and 4C are histogram plots of the number of breaths per 1000 breaths at various volumes Vt for narrow, medium, and wide distributions, respectively. The distribution functions vary the breath over a 1000 breath sequence and a histogram of the normalized volumes in cc/kg ideal body weight (IBW) as shown in FIGS. 4A, 4B, and 4C. These various distributions were used to simulate the operation of the second AVAPS method 300 as shown in FIG. 3. Each of the three distributions have a mean value of 8 cc/kg. The target volume Vtarget 305 should be normalized to this ratio. Note that in the medium and the wide distributions there are more large volumes selected than in the narrow distribution.

Figure 5A:
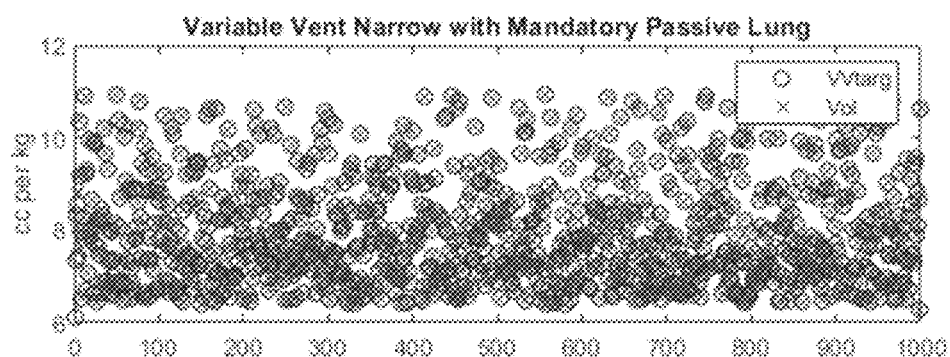
FIGS. 5A, 5B, and 5C illustrate simulated results of the second AVAPS method using the narrow distribution of FIG. 4A on a passive lung.
Figure 5B:
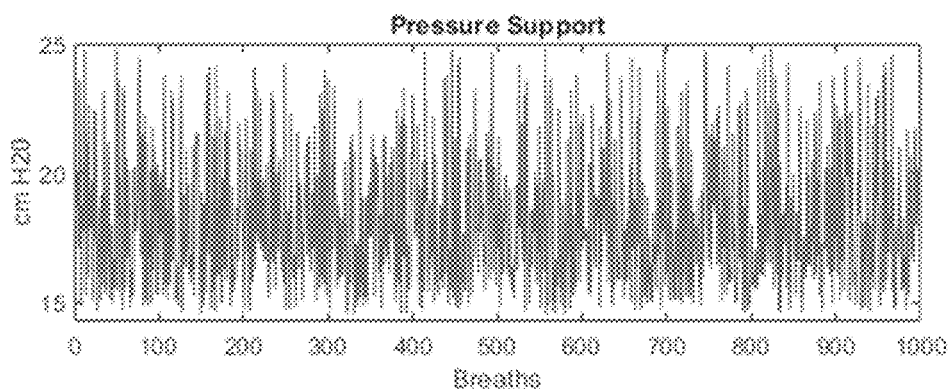
Figure 5C:
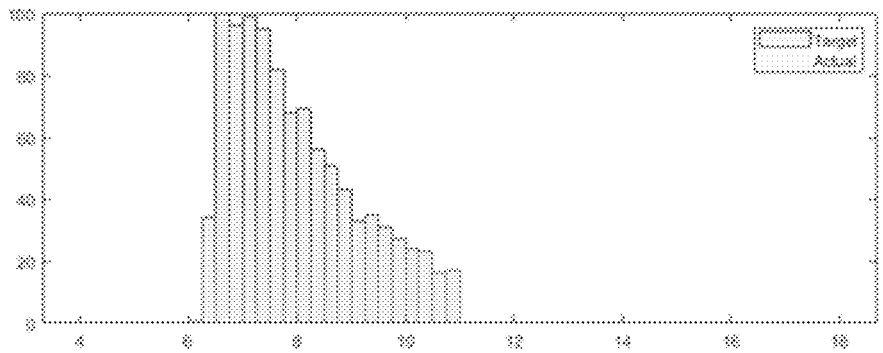

FIGS. 5A, 5B, and 5C illustrate simulated results of the second AVAPS method 300 using the narrow distribution of FIG. 4A on a passive lung. The following parameters were used in the simulation: R=20; C=20; and Vtarget=300 ml. FIG. 5A is a plot of normalized volume versus breath number for both the target VV (VVtarg) and the actual volume. VVtarg is represented by the circles on the plot, and the actual volume is shown by the x's on the plot. FIG. 5B is the pressure support provided by the second AVAPS method 300 on each breath. The pressure support varied from about 15 to about 25 cm H₂O. Also note that the values vary largely from breath to breath, and this is possible because three is no speed limit function in the second AVAPS method 300. As can be seen in this situation the measured volume matches the VVtarget very well as the circles and x's on the plot align very closely. FIG. 5C is a histogram of the number of breaths at each normalized measured lung volume. An analysis of this data shows that a mean tidal volume of 300.1 ml is obtained as compared to the Vtarget of 300 ml. The second AVAPS method 300 achieved the desired mean Vtarget value. Because a passive test lung was used, this is an easy situation for providing the needed pressure support to obtain the desired volume on each breath. The use of the passive lung does accurately model neuromuscular patients because they do not have a large respiratory drive.

It is noted that when the patient is active, the same control over the tidal volumes does not result as with the passive lung. But the second AVAPS method 300 can maintain the average tidal volume because of the extra control loop in the second AVAPS method 300.

Figure 6A:
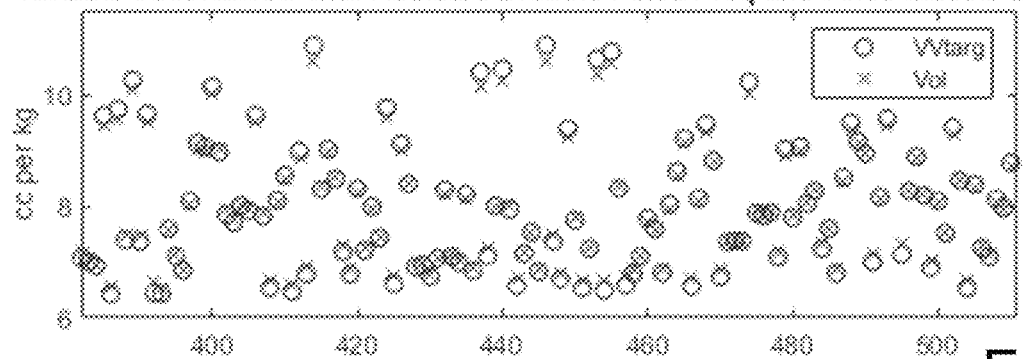
FIGS. 6A, 6B, and 6C illustrate simulated results of the second AVAPS method using the narrow distribution of FIG. 4A using assisted breaths with a fixed frequency and fixed muscle effort.
Figure 6B:
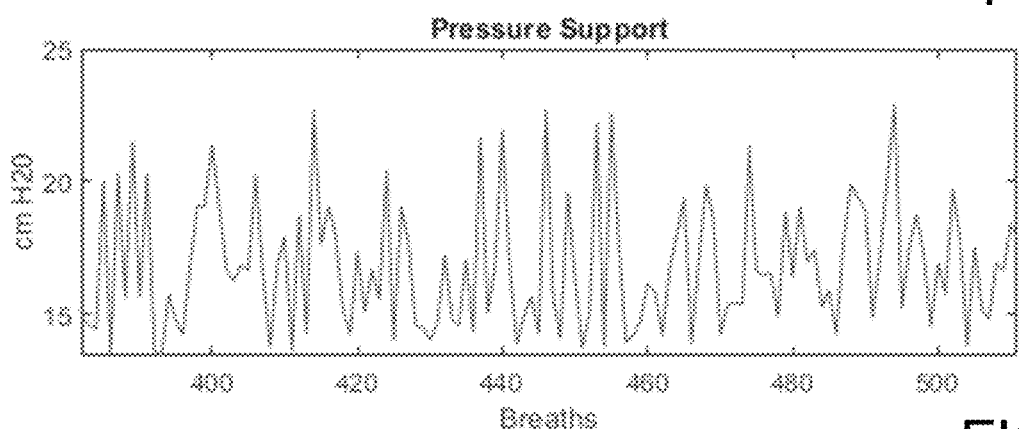
Figure 6C:
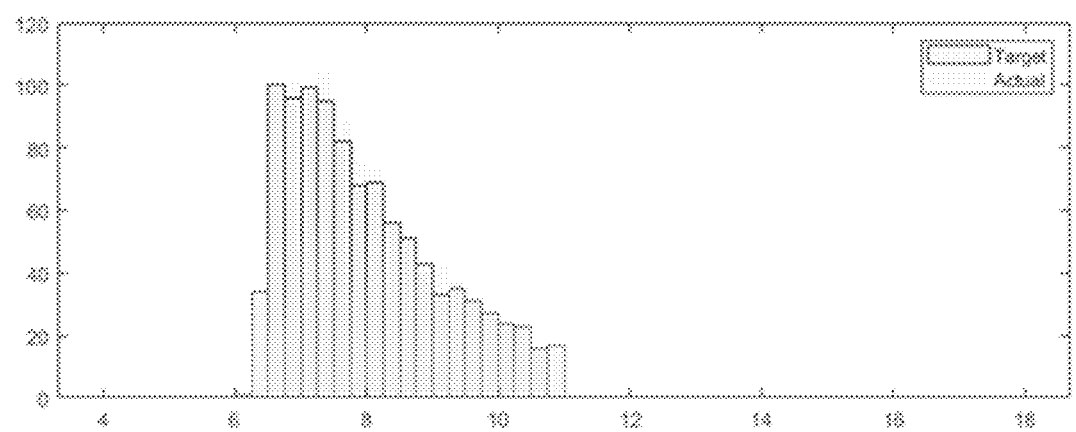

FIGS. 6A, 6B, and 6C illustrate simulated results of the second AVAPS method 300 using the narrow distribution of FIG. 4A using assisted breaths with a fixed frequency and fixed muscle effort. So in this situation the patient is taking some of the breaths on their own and being assisted on other breaths. The following parameters were used in the simulation: R=20; C=20; and Vtarget=300 ml. FIG. 6A is a plot of normalized volume versus breath number for both the target VV (VVtarg) and the actual volume. As before, VVtarg is represented by the circles on the plot, and the actual volume is shown by the x's on the plot. FIG. 6B is the pressure support provided by the second AVAPS method 300 on each breath. The pressure support varied from about 13 to about 23 cm $H_2O$. As can be seen in this situation, the measured volume is close to the VVtarget values, but there are some variation as can be seen where the circles and x's on the plot do not quite align. FIG. 6C is a histogram of the number of breaths at each normalized measured lung volume. An analysis of this data shows that a mean tidal volume of 300.3 ml is obtained as compared to the Vtarget of 300 ml. Again, the second AVAPS method 300 achieved the desired mean Vtarget value.

Figure 7A:
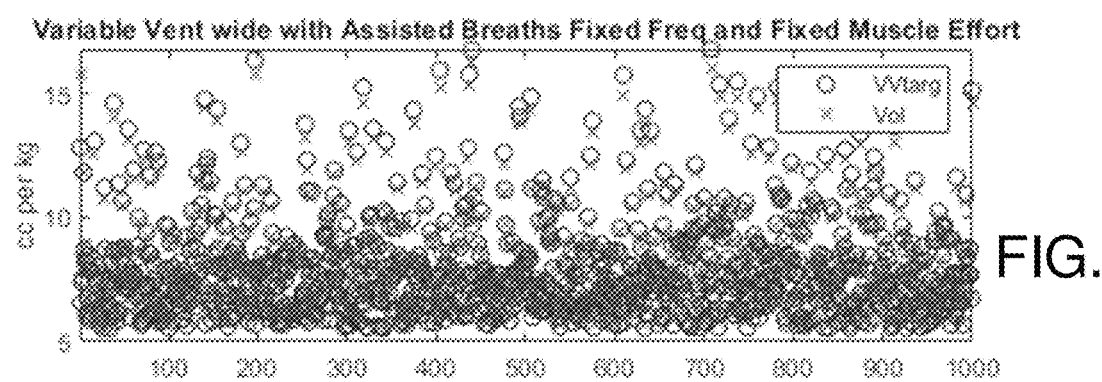
FIGS. 7A, 7B, and 7C illustrate simulated results of the second AVAPS method using the wide distribution of FIG. 4C using assisted breaths with a fixed frequency and fixed muscle effort.
Figure 7B:
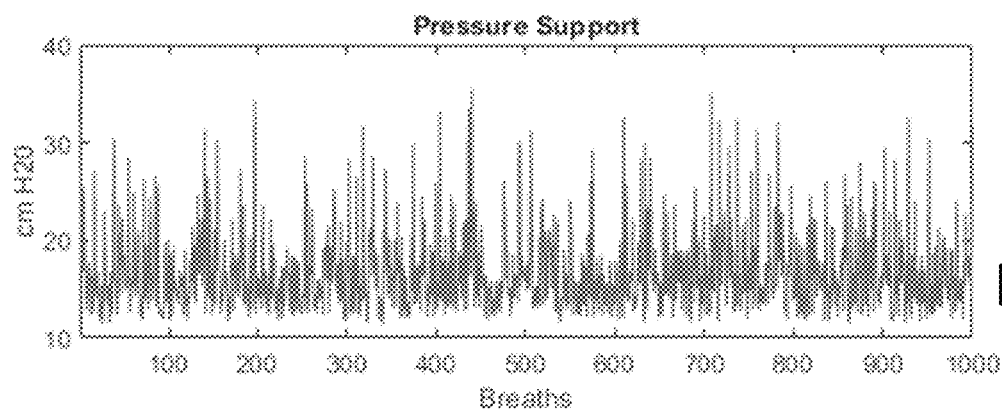
Figure 7C:
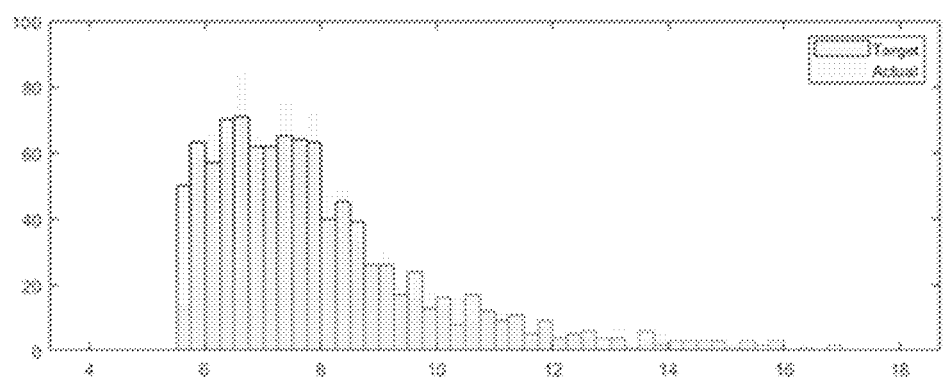

FIGS. 7A, 7B, and 7C illustrate simulated results of the second AVAPS method 300 using the wide distribution of FIG. 4C using assisted breaths with a fixed frequency and fixed muscle effort. So in this situation the patient is taking some of the breaths on their own and being assisted on other breaths. The following parameters were used in the simulation: R=20; C=20; and Vtarget=300 ml. FIG. 7A is a plot of normalized volume versus breath number for both the target VV (VVtarg) and the actual volume. As before, VVtarg is represented by the circles on the plot, and the actual volume is shown by the x's on the plot. FIG. 7B is the pressure support provided by the second AVAPS method 300 on each breath. The pressure support varied from about 11 to about 32 cm $H_2O$. As can be seen in this situation, the measured volume is close to the VVtarget values, but there are some variation as can be seen where the circles and x's on the plot do not quite align. FIG. 7C is a histogram of the number of breaths at each normalized measured lung volume. An analysis of this data shows that a mean tidal volume of 299.9 ml is obtained as compared to the Vtarget of 300 ml. Again, the second AVAPS method 300 achieved the desired mean Vtarget value.

Various other simulations using the different patient parameters and distributions showed that the mean Vtarget values was within 1 ml of the Vtarget value of 300. This illustrates that the second AVAPS method 300 achieves the desired mean tidal volume.

The second AVAPS method 300 may be implemented using hardware to carry out the specific functions shown in FIG. 3. This hardware may be an integrated circuit that receives the various input data and provides the control outputs to the ventilator.

Figure 8:
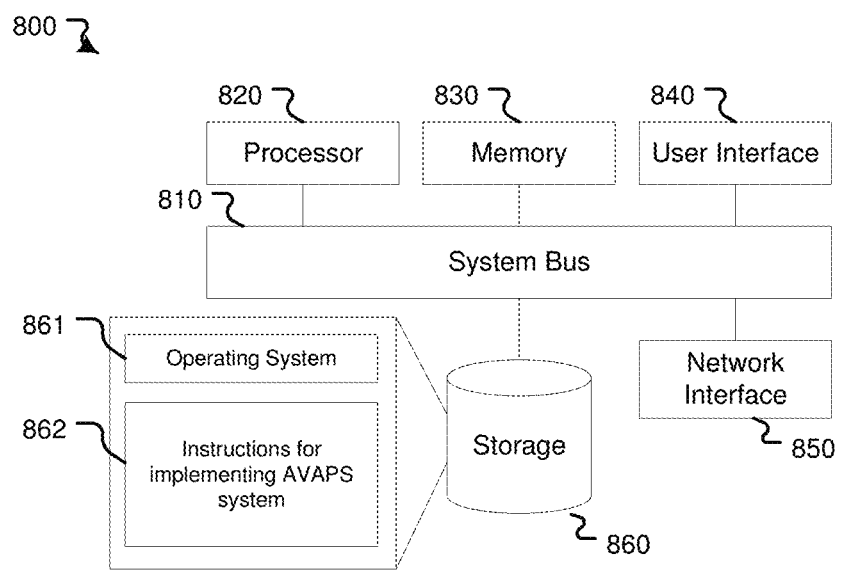
FIG. 8 illustrates an exemplary hardware diagram for implementing the second AVAPS method of FIG. 3.

The second AVAPS method 300 may also be implemented using a processor and software instructions on that processor to carry out the functions shown in FIG. 3. FIG. 8 illustrates an exemplary hardware diagram of a system 800 for implementing the second AVAPS method 300 of FIG. 3. As shown, the system 800 includes a processor 820, memory 830, user interface 840, network interface 850, and storage 860 interconnected via one or more system buses 810. It will be understood that FIG. 8 constitutes, in some respects, an abstraction and that the actual organization of the components of the system 800 may be more complex than illustrated.

The processor 820 may be any hardware device capable of executing instructions stored in memory 830 or storage 860 or otherwise processing data. As such, the processor may include a microprocessor, a graphics processing unit (GPU), field programmable gate array (FPGA), application-specific integrated circuit (ASIC), any processor capable of parallel computing, or other similar devices. The processor may also be a special processor that implements machine learning models.

The memory 830 may include various memories such as, for example L1, L2, or L3 cache or system memory. As such, the memory 830 may include static random-access memory (SRAM), dynamic RAM (DRAM), flash memory, read only memory (ROM), or other similar memory devices.

The user interface 840 may include one or more devices for enabling communication with a user and may present information to users. For example, the user interface 840 may include a display, a touch interface, a mouse, and/or a keyboard for receiving user commands. In some embodiments, the user interface 840 may include a command line interface or graphical user interface that may be presented to a remote terminal via the network interface 850.

The network interface 850 may include one or more devices for enabling communication with other hardware devices. For example, the network interface 850 may include a network interface card (NIC) configured to communicate according to the Ethernet protocol or other communications protocols, including wireless protocols. Additionally, the network interface 850 may implement a TCP/IP stack for communication according to the TCP/IP protocols. Various alternative or additional hardware or configurations for the network interface 850 will be apparent.

The storage 860 may include one or more machine-readable storage media such as read-only memory (ROM), random-access memory (RAM), magnetic disk storage media, optical storage media, flash-memory devices, or similar storage media. In various embodiments, the storage 860 may store instructions for execution by the processor 820 or data upon which the processor 820 may operate. For example, the storage 860 may store a base operating system 861 for controlling various basic operations of the system 800. The storage 860 may also store instructions 862 for implementing the first or second AVAPS methods 200, 300.

It will be apparent that various information described as stored in the storage 860 may be additionally or alternatively stored in the memory 830. In this respect, the memory 830 may also be considered to constitute a "storage device" and the storage 860 may be considered a "memory." Various other arrangements will be apparent. Further, the memory 830 and storage 860 may both be considered to be "non-transitory machine-readable media." As used herein, the term "non-transitory" will be understood to exclude transitory signals but to include all forms of storage, including both volatile and non-volatile memories.

While the system 800 is shown as including one of each described component, the various components may be duplicated in various embodiments. For example, the processor 820 may include multiple microprocessors that are configured to independently execute the methods described herein or are configured to perform steps or subroutines of the methods described herein such that the multiple processors cooperate to achieve the functionality described herein. Such plurality of processors may be of the same or different types. Further, where the system 800 is implemented in a cloud computing system, the various hardware components may belong to separate physical systems. For example, the processor 820 may include a first processor in a first server and a second processor in a second server.

The second AVAPS method 300 described herein provides a technological improvement over prior AVAPS methods by allowing for variable volume ventilation to be used along with AVAPS. As described above the use of variable volume ventilation has various benefits to the patient and combines these benefits with the benefits of AVAPS. Accordingly, a better ventilation therapy may be provided to the patient.

Any combination of specific software running on a processor to implement the embodiments of the invention, constitute a specific dedicated machine.

As used herein, the term "non-transitory machine-readable storage medium" will be understood to exclude a transitory propagation signal but to include all forms of volatile and non-volatile memory.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A method for controlling a ventilator to provide variable volume (VV) with average volume assured pressure support (AVAPS), comprising:
   producing a VV target volume using a VV distribution function;
   producing a volume error Verror that is the difference between the VV target volume and a measured volume of the previous breath;
   scaling the volume error Verror;
   producing a VV target difference as the difference between VV target volume and the VV target volume of the previous breath;
   producing a modified volume error by adding the VV target difference to the scaled volume error Verror;
   producing a delta pressure support ΔPS based upon the modified volume error and a dynamic compliance; and
   producing a current pressure support value based upon the delta pressure support ΔPS and the pressure support value of the previous breath.

2. The method of claim 1, wherein producing a delta pressure support ΔPS further comprises dividing the modified volume error by the dynamic compliance.

3. The method of claim 2, wherein the volume error Verror is scaled by a factor of 2.

4. The method of claim 1, further comprising limiting the current pressure support by a minimum pressure support value and a maximum pressure support value.

5. The method of claim 1, further comprising generating a breath profile based upon the current pressure support and a positive end-expiratory pressure (PEEP) value.

6. The method of claim 5, further comprising rise time filtering the breath profile.

7. The method of claim 6, further comprising applying the breath profile to a user's lung and measuring a volume of the resulting breath.

8. The method of claim 1, wherein the VV distribution function has a mean value based upon a received target volume value.

9. The method of claim 1, wherein the VV distribution function may be selected from a plurality of different VV distribution functions.

10. A controller configured to control a ventilator to provide variable volume (VV) with average volume assured pressure support (AVAPS), comprising:
    a memory;
    a processor coupled to the memory, wherein the processor is further configured to:
       produce a VV target volume using a VV distribution function;
       produce a volume error Verror that is the difference between the VV target volume and a measured volume of the previous breath;
       scale the volume error Verror;
       produce a VV target difference as the difference between VV target volume and the VV target volume of the previous breath;
       produce a modified volume error by adding the VV target difference to the scaled volume error Verror;
       produce a delta pressure support ΔPS based upon the modified volume error and a dynamic compliance; and
       produce a current pressure support value based upon the delta pressure support ΔPS and the pressure support value of the previous breath.

11. The controller of claim 10, wherein producing a delta pressure support ΔPS further comprises dividing the modified volume error by the dynamic compliance.

12. The controller of claim 11, wherein the volume error Verror is scaled by a factor of 2.

13. The controller of claim 10, wherein the processor is further configured to limit the current pressure support by a minimum pressure support value and a maximum pressure support value.

14. The controller of claim 10, wherein the processor is further configured to generate a breath profile based upon the current pressure support and a positive end-expiratory pressure (PEEP) value.

15. The controller of claim 14, wherein the processor is further configured to rise time filter the breath profile.

16. The controller of claim 15, wherein the processor is further configured to apply the breath profile to a user's lung and measuring a volume of the resulting breath.

17. The controller of claim 10, wherein the VV distribution function has a mean value based upon a received target volume value.

18. The controller of claim 10, wherein the VV distribution function may be selected from a plurality of different VV distribution functions.

* * * * *